United States Patent [19]
Ichikawa et al.

[11] Patent Number: 5,153,340
[45] Date of Patent: Oct. 6, 1992

[54] OIL-SOLUBLE N-LONG CHAINED ACYL ACIDIC AMINO ACID ESTER, MIXTURE THEREOF AND PERFUMING COSMETICS CONTAINING THE SAME

[75] Inventors: Tomomichi Ichikawa; Shigetoshi Fukami, both of Tokyo; Tohru Kobayashi, Kawasaki, all of Japan

[73] Assignee: Ajinomoto Co., Inc., Tokyo, Japan

[21] Appl. No.: 658,675

[22] Filed: Feb. 21, 1991

[30] Foreign Application Priority Data

Feb. 23, 1990 [JP] Japan ................................. 2-42762
Apr. 20, 1990 [JP] Japan ................................. 2-104460

[51] Int. Cl.$^5$ ........................... C07J 53/00; C07J 9/00
[52] U.S. Cl. ...................................... 552/509; 552/544
[58] Field of Search ............................... 552/509, 544

[56] References Cited

U.S. PATENT DOCUMENTS

| | | | |
|---|---|---|---|
| 2,264,888 | 12/1941 | Oppenauer | 552/509 |
| 4,588,717 | 5/1986 | Mitchell | 552/544 |
| 4,614,619 | 9/1986 | Shannon | 552/544 |

OTHER PUBLICATIONS

Chem. Abstracts, vol. 94, No. 12, Mar. 23, 1981, Columbua, Ohio, US; Abst. No. 86119W, K. Kodama: "Emulsifier Composition", p. 118, Column 1; See Abstract.
European Polymers Journal, vol. 21, No. 8, 1985, Oxford GB pp. 741-745; G. Quentin and A. Pleurdeau: "Polymere Support de Steroide a Bras Ecateur Peptidique" see p. 743.

Primary Examiner—Howard T. Mars
Assistant Examiner—Kimberly J. Kestler
Attorney, Agent, or Firm—Oblon, Spivak, McClelland, Maier & Neustadt

[57] ABSTRACT

Herein are disclosed (1) an oil-soluble N-long chained acyl acidic amino acid mono- or di-ester having at least one sterol ester in the molecule, which is a novel compound of excellent emulsifying and hydrating performances, (2) an oily composition consisting of or comprising a mixture of such esters, and (3) perfuming cosmetics blended with such ester or such oily composition.

1 Claim, No Drawings

OIL-SOLUBLE N-LONG CHAINED ACYL ACIDIC AMINO ACID ESTER, MIXTURE THEREOF AND PERFUMING COSMETICS CONTAINING THE SAME

BACKGROUND OF THE INVENTION

1. Field of the Invention

The present invention concerns an oil-soluble N-long chained acyl acidic amino acid ester having at least one sterol ester, an oily composition consisting of or comprising a mixture of such esters, as well as perfuming cosmetics prepared by blending such ester or such oily composition.

2. Description of the Prior Art

Various kinds of esters have generally been used as oleo-phase materials for skin and hair cosmetics and medicines for external application. Further, amino acid type surface active agents of natural origin and with high safety have often been used recently. By the way, most of such amino acid type surface active agents are hydrophilic and, as oil-soluble amino acid type surface active agent usable as the oleo-phase material for perfuming cosmetics, etc., N-lower acyl acidic amino acid diesters, N-long chained acyl acidic amino acid diesters, N-long chained acyl neutral amino acid ester and N,N-dilong chained acyl basic amino acid esters and the like have been known.

However, although the known compounds as described above have some degree of emulsifying and hydrating performances, both of the performances are remarkably low in the N-long chained acyl acidic amino acid higher alcohol diesters, and more excellent high performances are required for the improvement of the performance, for example, of perfuming cosmetics.

On the other hand, various kinds of sterol esters have hitherto been used as the oleo-phase material having the excellent emulsifying performance and further of excellent moisture permeability because of its melting point of 35°~40° C. near the body temperature. Excellent moisture permeability prevents the skin blocking caused by cosmetics. They have particularly preferred hydrating performance but involve a drawback that the use of products gives somewhat heavy feeling when they are blended with perfuming cosmetics.

OBJECT AND SUMMARY OF THE INVENTION

An object of the present invention is to provide an oil-soluble N-long chained acyl acidic amino acid mono- or di-ester having at least one sterol ester in the molecule, which is a novel compound of excellent emulsifying and hydrating performances.

Another object of the present invention is to provide an oily composition consisting of or comprising a mixture of such esters.

A further object of the present invention is to provide perfuming cosmetics blended with such ester or such oily composition as described above.

DETAILED DESCRIPTION OF THE PREFERRED EMBODIMENT

Referring more specifically, the first aspect of the present invention resides in an N-long chained acyl acidic amino acid mono- or di-ester, which is oil-soluble and represented by the following general formula (I):

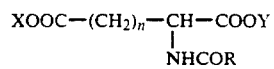

in which each of X and Y, which may be identical with or different from each other, represents an ester forming residue of a sterol, or one of X and Y represents an ester forming residue of a sterol and the other of them represents H or an ester forming residue of a liquid higher alkyl or alkenyl mono-hydric alcohol with 8 to 30 carbon atoms or an ester forming residue of a solid higher alkyl mono-hydric alcohol with 12 to 38 carbon atoms, COR represents a long chained acyl group with 8 to 22 carbon atoms and n is 1 or 2.

The N-long chained acyl acidic amino acid moiety of the ester according to the present invention represented by the general formula (I) is an N-long chained acyl aspartic acid (n=1 in the formula (I)) or N-long chained acyl glutamic acid (n=2 in the formula (I)), in which the long chained acyl group may be an acyl group derived from a saturated or unsaturated fatty acid with 8 to 22 carbon atoms, for example, an acyl group of a fatty acid of a single ingredient such as lauric acid, palmitic acid, stearic acid and oleic acid, as well as an acyl group of mixed fatty acids obtained from natural products such as palm oil fatty acid, tallow fatty acid and hardened tallow fatty acid and an acyl group of synthetic fatty acids (including branched fatty acids). Such long chained acyl groups are adopted for the acyl group with an aim of providing a hydrophobic property. The acidic amino acid moiety may be of an optically active form or a racemic form.

As the sterol, there can be mentioned, for example, cholesterol, phytosterol and hydrogenation product thereof (which may be of animal or vegetable origin). As the liquid higher alkyl or alkenyl alcohol with 8 to 30 carbon atoms, there can be exemplified a natural or synthetic aliphatic alcohol with 8 to 30 carbon atoms, which is liquid at normal temperature, for example, branched alcohol such as 2-octyl dodecyl alcohol and, in addition, unsaturated alcohol such as oleyl alcohol. Then, as the solid higher alkyl alcohol with 12 to 38 carbon atoms, there can be mentioned a saturated monohydric alcohol with 12 to 38 carbon atoms, which is solid at normal temperature, for example, cetyl alcohol and behenyl alcohol.

The ester represented by the general formula (I) of the present invention can be prepared by reacting an N-long chained acyl acidic amino acid and a sterol and, if necessary, a liquid higher alkyl or alkenyl monohydric alcohol with 8 to 30 carbon atoms or a solid alkyl monohydric alcohol with 12 to 38 carbon atoms by a generally known esterifying method, for example, (1) condensating dehydration by heating (under normal or reduced pressure), (2) ester-exchanging reaction, (3) condensating dehydration under azeotropic boiling or the like. In particular, preparation by condensation dehydration under azeotropic boiling is optimum in view of reaction conditions, and yield and purity of the products.

Referring more specifically, for the sterol di-ester in which both of X and Y are the ester forming residues of sterol, 20~22 mols of sterol based on one mol of the N-long chained acyl acidic amino acid and 10 to 50% of a non-polar solvent such as benzene or toluene (% by volume based on the charged amount of the N-long chained acyl acidic amino acid and the alcohol) are charged and sufficiently stirred and mixed in a reaction vessel and, subsequently, 0.01 to 1.5 mol of an acidic catalyst such as sulfuric acid, o-toluene sulfonic acid, hydrogen chloride or strongly acidic ion exchange resin is added and stirred under heating at 70° to 200° C. for 1 to 10 hours. In this case, the reaction is promoted by removing the water by-produced during the reaction as much as possible.

For the sterol mono-ester in which only one of X and Y is an ester forming residue of a sterol, while the other of them is H, the preparation method is similar to that for the sterol di-ester except for reducing the amount of the sterol used to one-half relative to the N-long chained acyl acidic amino acid. Preparation is of course not restricted only to the above-mentioned method but any of methods may be used so long as the N-long chained acyl acidic amino acid mono- or di-ester is finally derived, for example, a method of reacting an acidic amino acid at first with a sterol in the presence of an acidic catalyst into the corresponding acidic amino acid mono- or di-ester, which is then acylated into an N-long chained acyl form by a so-called Schotten Bauman reaction in which the mono- or di-ester is reacted with a long chained fatty acid halide in the presence of a basic catalyst.

For the mixed ester in which one of X and Y is an ester forming residue of a sterol and the other of them is an ester forming residue of a liquid or solid higher mono-hydric alcohol, an N-long chained acyl acidic amino acid, 2.0 to 2.2 mol of a sterol-containing mixed alcohol (the sterol and the higher mono-hydric alcohol may be in an equi-molar mixing ratio) based on one mol of the N-long chained acyl acidic amino acid and 10 to 50% of a solvent such as benzene or toluene (% by volume based on the charged amount of the N-long chained acyl acidic amino acid and the alcohol) are charged in a reaction vessel and mixed under stirring sufficiently and, subsequently, 0.01 to 1.5 mol of an acidic catalyst is added and stirred under heating at 70° to 200° C. for 1 to 10 hours. In this case, the reaction is promoted by removing the water by-produced during the reaction as much as possible. Preparation method is of course not restricted only to the above-mentioned method but any of methods may be used so long as the N-long chained acyl acidic amino acid mixed di-ester is finally derived, for example, a method of reacting at first an acidic amino acid with the sterol-containing mixed alcohol as described above in the presence of an acidic catalyst into the corresponding acidic amino mixed di-ester, which is then acylated into an N-long chained acyl form by a so-called Schotten Bauman reaction in which the mixed diester is reacted with a long chained fatty acid halide in the presence of a basic catalyst.

The aimed-at ester can be isolated from the ester reaction mixture by a customary method such as column chromatography.

An N-long chained acyl acidic amino acid ester or a mixture thereof according to the present invention represented by the general formula (I) synthesized by the method described above may be modified variously in accordance with the purpose of use, that is, those having liquid to solid nature and those having low to high viscosity depending on the difference of the acyl group, or depending on the composition in a case of using a sterol-containing alcohol mixture as the alcohol.

The N-long chained acyl acidic amino acid ester according to the present invention has a feature capable of improving the emulsifying performance and the hydrating performance, which are insufficient in conventional higher alcohol di-ester of N-long chained acyl acidic amino acid, by introducing a sterol into the ester portion, improving viscous and heavy feeling in the conventional sterol ester and providing affinity and emollient property to skin and hair. The ester is also capable of giving perfuming cosmetics excellent moisture permeability when incorporated therein.

The hydrating property of the oil-soluble N-long chained acyl acidic amino acid ester according to the present invention is shown in Table 1. As apparent from Table 1, the ester mixtures according to the present invention (specimens Nos. 1~15. The specimens Nos. 1~15 are the same as specimens Nos. 1~15 in Table 2, respectively.) have more excellent hydrating power, form firm W/O type emulsion and, accordingly, have strong emulsifying power as compared with existent N-long chained acyl acidic amino acid higher alcohol diester and polyoxyalkylene higher alcohol ether di-ester of N-long chained acyl acidic amino acid. Liquid paraffin and vaseline which have originally no hydrating power show excellent hydrating power when blended with a small amount of an ester of the present invention, i.e., the ester can improve hydrating power of liquid paraffin and vaseline.

The excellent moisture permeability of the oil-soluble N-long chained acyl acidic amino acid ester according to the present invention is shown in Table 1a. It can be seen from the table that perfuming cosmetics comprising an ester of the present invention do not prevent normal skin metabolism such as unperceivable sweating and skin breathing, and that vaseline which is originally poor in moisture permeability is improved in that property when blended with an ester of the present invention.

TABLE 1

Hydrating property of amino acid type sterol ester

| Specimen | Hydrating property (%)* | Specimen | Hydrating property (%)* |
| --- | --- | --- | --- |
| No. 1 | 429.3 | No. 11 | 453.4 |
| No. 2 | 365.2 | No. 12 | 752.3 |
| No. 3 | 510.4 | No. 13 | 853.1 |
| No. 4 | 523.5 | No. 14 | 440.2 |
| No. 5 | 599.0 | No. 15 | 873.6 |
| No. 6 | 514.9 | A 1:9 mixture of Spec. No. 3 and liquid paraffin | 500 |
| No. 7 | 624.4 | A 1:9 mixture of Spec. No. 3 and vaseline | 430 |
| No. 8 | 474.7 | N-lauroyl glutamic acid di-2-octyldodecyl ether | 88.4 |
| No. 9 | 419.6 | N-lauroyl glutamic acid di-POE(2 mol)-octyldodecyl ether | 123.1 |
| No. 10 | 443.8 | N-lauroyl glutamic acid di-POE(5 mol)-octyldodecyl ether | 129.0 |
| | | N-lauroyl glutamic acid di-POE(2 mol)-stearyl ether | 183.2 |
| | | N-lauroyl glutamic acid di-POE(5 mol)-stearyl ether | 189.6 |

*100 g of specimen is sufficiently stirred under gradual addition of ion exchanged water to form a W/O type emulsion and the hydrating power is defined as a maximum amount of water added that can be emulsified into the W/O type emulsion.

TABLE 1a

| Moisture permeability | |
| --- | --- |
| Specimen | Moisture permeability (%)** |
| No. 3 | 13.0 |

TABLE 1a-continued

| Specimen | Moisture permeability (%)** |
| --- | --- |
| Lanolin | 5.5 |
| Vaseline | 1.3 |
| a 1:1 mixture of Spec. No. 3 and vaseline | 6.3 |

**A specimen is spread in an amount of 0.9 mg/cm² on a circular sheet (7 cm in diameter) of cellophane and the cellophane sheet is put on a moisture permeable cup (JIS Z-0208). The cup is let stand under an atmosphere of R.H. 90% at 25° C. for 24 hours. The moisture permeability is determined on the weight change in the water content, and, however, standardized by comparing with the case of an unspread cellophane sheet similarly processed as control, its moisturepermeability being 100%.

Now, the present inventors have made an earnest study, taking notice on the emulsifying and hydrating performance of the sterol esters represented by the general formula (I), developed an amino acid type oleophase material having excellent emulsifying and hydrating performances and free from heavy feeling of use which is the drawback of the sterol ester and has accomplished the present invention in the second to the fourth aspects.

The second aspect of the present invention concerns an oily sterol composition comprising an oil-soluble N-long chained acyl acidic amino acid mono- and/or di-ester (group C ester) represented by the general formula (I), and at least 5 mol% of an oil-soluble N-long chained acyl acidic amino acid di-ester (group Ca ester) represented by the following general formula (Ia):

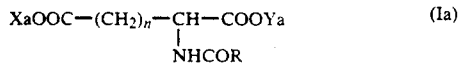
(Ia)

where one of Xa and Ya represents an ester forming residue of a sterol, the other of them represents an ester forming residue of a liquid higher alkyl or alkenyl mono-hydric alcohol with 8 to 30 carbon atoms, and COR and n have respectively the same meanings as those in the general formula (I) described above.

Such an oily ester composition can be obtained, for example, by the following procedure. That is, an ester belonging to the group Ca ester is prepared by a preparation method for the group C ester, to which an ester belonging to the group C ester but not belonging to the group Ca ester is added at such a ratio that the former is contained at least by 5 mol%.

The third aspect of the present invention concerns an oily composition comprising:

(1) an oil-soluble N-long chained acyl acidic amino acid mono- and/or di-ester represented by the general formula (I) described above (group C ester) and (2) at least one ester selected from the group consisting of mono- and/or di-esters represented by the below-given general formula (II) (group A ester), mono- and/or di-esters represented by the below-given general formula (III) (group B ester) and di-esters represented by the below-given general formula (IV) and/or (IVa) (group D ester), and containing at least 5 mol% of the group C ester represented by the above-described general formula (I).

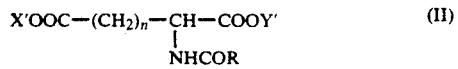
(II)

where each of X' and Y', which may be identical with or different from each other, represents an ester forming residue of a liquid higher alkyl or alkenyl mono-hydric alcohol with 8 to 30 carbon atoms, or one of them is an ester forming residue of a liquid higher alkyl or alkenyl mono-hydric alcohol with 8 to 30 carbon atoms, while the other of them represents H, and n and COR have respectively the same meanings as those in the general formula (I).

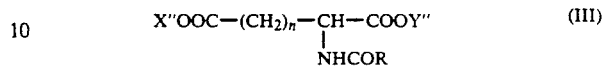
(III)

where each of Xa" and Y", which may be identical with or different from each other, represents an ester forming residue of a solid alkyl mono-hydric alcohol with 12 to 38 carbon atoms, or one of X" and Y" represents an ester forming residue of a solid alkyl mono-hydric alcohol with 12 to 38 carbon atoms, while the other of them represents H, and n and COR have respectively the same meanings as those in the general formula (I).

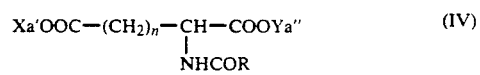
(IV)

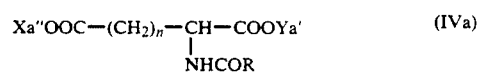
(IVa)

where each of Xa' and Ya', which may be identical with or different from each other, represents an ester forming residue of a liquid higher alkyl or alkenyl mono-hydric alcohol with 8 to 30 carbon atoms, each of Xa" and Ya", which may be identical with or different from each other, represents an ester forming residue of a solid alkyl mono-hydric alcohol with 12 to 38 carbon atoms, and n and COR have respectively the same meanings as those in the general formula (I).

The synthesis method for the esters represented by the general formula (I) (group C ester) has already been explained.

The esters represented by the general formula (II) (group A ester) and the esters represented by the general formula (III) (group B ester) may be synthesized by known methods.

The mixed di-esters of the alkyl alcohol and the alkenyl alcohol represented by the general formulae (IV) and (IVa) (group D ester) may also be synthesized by known methods.

It has been found by the present inventors that a remarkable effect can be obtained by an oily composition comprising a mixture of an ester belonging to the group C ester and at least one ester selected from the group consisting of esters belonging to the group A ester, group B ester and group D ester, in which the ratio of the group C ester in the mixture is at least 5 mol%.

The fourth aspect of the present invention resides in perfuming cosmetics comprising the ester of the first aspect or the oily composition according to the second or third aspect of the present invention.

In a case of incorporating the ester or the oily composition according to the present invention into perfuming cosmetics, it can be used by blending as a substitute for an oily substrate, for example, animal and vegetable oils such as squalane, castor oil, bee wax, lanoline, jojoba oil, carnauba wax, tung oil, sesami oil, evening primerose oil, palm oil and minc oil; mineral oils such as solid paraffin, silicone oil, sericin, liquid paraffin or vaseline; synthetic oils such as isopropylmyristate and synthetic polyether; and emollient agents such as stearic acid cholesteryl ester and hydroxystearic acid cholesteryl ester, or in combination with some of such oily substrates.

The present inventors have found that when the ester or oily composition as described above is incorporated into skin cosmetics such as face washing cream, face washing foam, cleansing cream, massage cream, cold cream, moisture cream, milky lotion, cosmetic liquid, pack, men's skin cosmetics and baby's skin protector, it can provide particularly excellent performance in the functions and in the emulsifying property as the oily substrate and can provide an emulsion product with excellent skin affinity, since it contains a sterol ester different from higher alcohol diester of N-long chained acyl acidic amino acid.

At the same time, the following facts have also been found; (i) If some conventional sterol ester other than the sterol ester of N-long chained acyl acidic amino acid is incorporated into an emulsion product, it has a drawback of giving heavy feeling of use to the product, whereas an emulsion product having extremely smooth feeling of use can be obtained in a case of using the ester or the oily composition according to the present invention as described above, (ii) The ester and the oily composition according to the present invention have no sensitivity and are oleo-phase materials having high safety, (iii) When the ester or the oily composition according to the present invention is incorporated, in particular, into foundation cosmetics or make-up cosmetics such as foundation cream, foundation lotion, face powder, lip rouge, lip cream, cheek rouge, eye make-up, eyebrow pencil, eyelash cosmetics, or nail cosmetics, anti-santan cosmetics, perfume or an eau de cologne, it is possible to provide products with preferred dispersibility of dyes, good spreadability, high water repellency and not being removed by sweat, (iv) When it is used for a hair caring product such as hair cream, perfumed oil, hair liquid, pomade, stick pomade, liquid hair conditioner, set lotion, treatment, hair tonic, hair spray or hair color, it can provide hairs with softness and luster, (v) When it is incorporated into aerosol products, a one liquid phase product having good compatibility with a spraying agent such as LPG can be prepared, and (vi) When it is added, for example, to shampoo, rinse, soap, bath cosmetics, shaving cosmetics, it can provide shampoo or rinse with strong hair affinity and conditioning effect, since this is an amino acid derivative, thereby giving moistened feeling, while it can provide soap, bath cosmetics and having cosmetics an effect of leaving oil content after use to protect skins against roughing. The fourth aspect of the present invention is based on such findings.

Surface active agents that can be blended with or incorporated into the perfuming cosmetics is one or a mixture of two or more of surface active agents selected from the group consisting of various kinds of surface active agents, for example, anionic surface active agents such as N-long chained fatty acid acyl glutamic acid salts, N-long chained fatty acid acyl sarcosine salts, N-long chained fatty acid acyl-N-methyl taurine salts, N-acyl-N-methyl-β-alanininate alkyl sulfate, alkyl benzene sulfonate, alkyloxy sulfonate, fatty acid amide ether sulfate, fatty acid salts, sulfosuccinic acid higher alcohol ester salts, polyoxyethylene alkyl sulfates, alkyl phosphates, isethionic acid fatty acid esters and alkyl ether carboxylates; nonionic surface active agents, for example, of an ether type such as glycerine ether and polyoxyethylene ether thereof, ether ester type such as polyoxyethylene ether of glycerine ester and polyoxyethylene ether of sorbitane ester, ester type such as polyoxyethylene fatty acid esters, glycerine esters, sorbitane esters and sucrose fatty acid esters and nitrogen-containing type such as fatty acid alkanol amides and polyoxyethylene fatty acid amides; cationic surface active agents, for example, aliphatic amine salts such as alkyl ammonium chlorides and dialkyl ammonium chlorides, quarternary ammonium salts thereof, aromatic quaternary ammonium salt such as benzalconium salt and fatty acid acyl alginic esters; as well as amphoteric surface active agents, for example, of a betaine type such as carboxy betaine, amino carboxylic acid type, and imidazoline derivatives.

As the aqueous phase ingredient, there can be mentioned polyhydric alcohols such as glycerine, ethylene glycol and 1,3-butylene glycol; water-soluble high polymers such as polyethylene glycol, alginate, carboxymethyl cellulose, hyaluronic acid, water-soluble chitin and sodium polyglutamate; sugar alcohol such as sorbitol and mannitol, and EO or PO addition adducts thereof; organic acids such as citric acid, succinic acid, lactic acid and PCA, and salts thereof, as well as lower alcohols such as ethanol and propanol.

As the powdery ingredient, there can be mentioned inorganic powders such as talc, kaoline, titanium dioxide and mica sericite, as well as organic powders such as N-mono-long chained acyl basic amino acids, guanine and laminate resin pearl.

The perfuming cosmetics according to the present invention can further contain customary cosmetic aids, for example, whitening agent, thickening agent, softening agent, moistening agent, fatting agent, moderating agent, wetting agent, preserving agent, UV absorber, chemicals, defoaming agent, chelating agent, protection colloid, perfume, colorant, or optional ingredients ordinarily used for cosmetics.

The amount of the ester or the oily composition according to the present invention added to perfuming cosmetics is such an amount that the addition effect of the ester or the oily composition according to the present invention can be attained in each of perfuming cosmetics and it can be determined easily by those skilled in the art.

The ester mixture according to the present invention can be used also as an oleo-phase starting material for medicines for external application.

EXAMPLE

The present invention will now be explained more specifically referring to preparation examples, blending examples and application examples (preparation examples for perfuming cosmetics).

Preparation Example 1

Synthesis of N-lauroyl-L-glutamic acid monocholesterol ester (A) (group C ester)

Into a 1000 ml flask, 165 g (0.5 mol) of N-lauroyl-L-glutamic acid and 300 ml of toluene were charged and, further, 194 g (0.5 mol) of cholesterol (manufactured by Riken Vitamine Co.) was added. Subsequently, 0.5 ml of sulfuric acid was added as a catalyst, and the mixture was heated to 130°~140° C. to carry out esterifying reaction for about 4 hours.

After repeating water washing, toluene was removed by distillation, to obtain 320 g of a waxy product. The product had an acid value of 82.4 and a saponification value of 161.3 and it can be seen that the product was a mono-ester.

Preparation Example 2

Synthesis of N-lauroyl-L-glutamic acid dicholesterol ester (B) (group C ester)

Quite in the same procedures as those in the esterifying reaction of Preparation Example 1 except for using 406 g (1.05 mol) of cholesterol, 480 g of an oily product was obtained.

The product had an acid value of 4.52 and a saponification value of 105.2 and it can be seen that the product was a di-ester.

Preparation Example 3

Synthesis of N-lauroyl-L-glutamic acid-α-cholesterol, ω-behenyl alcohol di-ester (C) (group Ca ester)

Quite in the same procedures as those in the esterifying reaction of Preparation Example 1 except for using 203 g cholesterol and 169 g of behenyl alcohol (manufactured by Kao Corporation), 483 g of a waxy product was obtained.

The product had an acid value of 0.48 and a saponification value of 117.6 and it can be seen that the product was a di-ester.

Preparation Example 4

Synthesis of N-lauroyl-L-glutamic acid-α-cholesterol, ω-2-octyl dodecanol di-ester (D) (group C ester)

Quite in the same procedures as those in the esterifying reaction of Preparation Example 1 except for using 203 g of cholesterol and 156 g of octyl dodecanol (manufactured by Shin-Nippon Rika Co.), 463 g of a waxy product was obtained.

The product had an acid value of 3.76 and a saponification value of 113.6 and it can be seen that the product was a di-ester.

Preparation Example 5

Synthesis of N-stearoyl-L-glutamic acid-α-cholesterol, ω-behenyl alcohol di-ester (E) (group Ca ester)

In the same procedures as those in the esterifying reaction in Preparation Example 1, 480 g of a waxy product was obtained by using 203 g of N-stearoyl-L-glutamic acid instead of N-lauroyl-L-glutamic acid and using 203 g of cholesterol and 169 g of behenyl alcohol.

The product had an acid value of 2.56 and a saponification value of 105.2, and it can be seen that the product was a di-ester.

Preparation Example 6

Synthesis of N-stearoyl-L-glutamic acid-α-cholesterol, ω-2-octyldodecanol di-ester (F) (group C ester)

In the same procedures as those in the esterifying reaction in Preparation Example 1, 495 g of a viscous liquid product was obtained by using 203 g of N-stearoyl-L-glutamic acid instead of N-lauroyl-L-glutamic acid and using 203 g of cholesterol and 156 g of 2-octyldodecanol.

The product had an acid value of 3.23 and a saponification value of 107.5 and it can be seen that the product was a di-ester.

Preparation Example 7

Synthesis of N-lauroyl-L-glutamic acid-α-dihydrocholesterol mono-ester (G) (group C ester)

Quite in the same procedures as those in the esterifying reaction of Preparation Example 1, 328 g of a waxy product was obtained by using 204 g of dihydrocholesterol instead of cholesterol.

The product had an acid value of 83.4 and a saponification value of 1642, and it can be seen that the product was a mono-ester.

Preparation Example 8

Synthesis of N-lauroyl-L-glutamic acid-α-dihydrocholesterol, ω-behenyl alcohol di-ester (H) (group Ca ester)

Quite in the same procedures as those in the esterifying reaction of Preparation Example 1, 473 g of a soft pasty product was obtained by using 204 g of dihydrocholesterol and 169 g of behenyl alcohol instead of cholesterol.

The product had an acid value of 3.11 and a saponification value of 111.6 and it can be seen that the product was a di-ester.

Preparation Example 9

Synthesis of N-lauroyl-L-glutamic acid-phytosterol monoester (I) (group C ester)

Quite in the same procedures as those in the esterifying reaction of Preparation Example 1, a product was obtained by using 215 g of phytosterol (manufactured by Eizai Co.) instead of cholesterol.

The product had an acid value of 80.4 and a saponification value of 159.4, and it can be seen that the product was a mono-ester.

Preparation Example 10

Synthesis of N-lauroyl-L-glutamic acid-α-phytosterol, ω-behenyl alcohol diester (H) (group Ca ester)

Quite in the same procedures as those in the esterifying reaction of Preparation Example 1, a product was obtained by using 215 g of phytosterol and 169 g of behenyl alcohol instead of cholesterol.

The product had an acid value of 4.25 and a saponification value of 109.4, and it can be seen that the product was a mono-ester.

Preparation Example 11

Synthesis of N-lauroyl-L-glutamic acid-α-dihydrocholesterol, ω-2-octyldodecanol di-ester (K) (group C ester)

Quite in the same procedures as those in the esterifying reaction of Preparation Example 1, 473 g of a pasty product was obtained by using 204 g of dihydrocholesterol and 156 g of 2-octyldodecanol instead of cholesterol.

The product had an acid value of 2.03 and a saponification value of 115.3, and it can be seen that the product was a mono-ester.

Preparation Example 12

Synthesis of N-lauroyl-L-glutamic acid-α-phytosterol, ω-2-octyldodecanol di-ester (L) (group C ester)

Quite in the same procedures as those in the esterifying reaction of Preparation Example 1, 483 g of a pasty product was obtained by using 215 g of phytosterol and 156 g of 2-octyldodecanol instead of cholesterol.

The pasty product had an acid value of 2.34 and a saponification value of 112.1, and it can be seen that the product was a mono-ester.

Preparation Example 13

Synthesis of N-lauroyl-L-glutamic acid behenyl alcohol mono-ester (M) (group B ester)

Quite in the same procedures as those in the esterifying reaction of Preparation Example 1, 301 g of a waxy product was obtained by adding 169 g of behenyl alcohol instead of cholesterol.

The product had an acid value of 89.57 and a saponification value of 179.3, and it can be seen that the product was a mono-ester.

Preparation Example 14

Synthesis of N-lauroyl-L-glutamic acid behenyl alcohol di-ester (N) (group B ester)

443.5 g of a waxy product was obtained by using 338 g of behenyl alcohol in the esterifying reaction of Preparation Example 13.

The product had an acid value of 1.28 and a saponification value of 117 6, and it can be seen that the product was a di-ester.

Preparation Example 15

Synthesis of N-lauroyl-L-glutamic acid-α-2-octyldodecyl alcohol mono-ester (O) (group A ester)

288 g of a product was obtained by using 156 g of 2-octyldodecanol instead of behenyl alcohol in the esterifying reaction of Preparation Example 13.

The product had an acid value of 93.23 and a saponification value of 184.0, and it is found that the product was a mono-ester.

Preparation Example 16

Synthesis of N-lauroyl-L-glutamic acid-α-2-octyldodecyl alcohol di-ester (P) (group A ester)

406.7 g of a product was obtained by using 313 g of 2-octyldodecyl alcohol in the esterifying reaction of Preparation Example 15.

The product had an acid value of 3.57 and a saponification value of 127.4, and it is found that the product was a di-ester.

Preparation Example 17

Synthesis of N-lauroyl-L-glutamic acid-α-behenyl alcohol, ω-2-octyldodecyl alcohol di-ester (Q) (group D ester)

447 g of a product was obtained by further adding 156 g of 2-octyldodecanol in the esterifying reaction of Preparation Example 13.

The product had an acid value of 3.74 and a saponification value of 123.8 and it is found that the product was a di-ester.

Preparation Example 18

One mol of N-lauroyl-L-glutamic acid and an alcohol mixture (0.6 mol of cholesterol, 1 mol of 2-octyldodecyl alcohol and 0.4 mol of behenyl alcohol) were charged in a reaction vessel, to which 200 ml of toluene was added as a solvent. Then, the reaction mixture was stirred under heating, to which 1 mol of $H_2SO_4$ was added as a catalyst, and the mass was brought into reaction by continuing stirring and heating at 90°~140° C. for about 4 hours. Meanwhile, the by-produced water was sufficiently removed.

After the completion of the reaction, the reaction mixture was neutralized with an aqueous solution of potassium hydroxide and the solvent toluene was recovered to obtain an aimed-at mixture of three kinds of esters (specimen No. 19).

Yield=98.2%, acid value=3.06, saponification value=121.87, pH (1%)=5.55, the molar ratio of the group A ester, group B ester and group C ester (%)=0:20:30.

Preparation Example 19

One mol of N-lauroyl-L-glutamic acid and an alcohol mixture (0.6 mol of phytosterol, 1.2 mol of 2-octyldodecyl alcohol and 0.2 mol of behenyl alcohol) were charged in a reaction vessel and the content was melted under stirring and heating. Then, 1 ml of $H_2SO_4$ was added as a catalyst and the mass was brought into reaction under a nitrogen atmosphere by continuing stirring and heating at 100°~140° C. for about 5 hours.

After the completion of the reaction, the reaction mixture was neutralized with an aqueous solution of potassium hydroxide to obtain an aimed-at mixture of three kinds of esters (specimen No. 20).

Yield=98.0%, acid value=4.25, saponification value=106.23, pH (1%)=5.58, the molar ratio of the group A ester, group B ester and group C ester (%)=60:10:30.

Preparation Example 20

One mol of N-lauroyl-L-glutamic acid and an alcohol mixture (0.5 mol of cholesterol and 1.5 mol of 2-octyldodecyl alcohol) were charged in a reaction vessel, to which 200 ml of toluene was added as a solvent, to which 0.05 mol of p-toluene sulfonic acid was added as a catalyst, and the mixture was brought into reaction by continuing stirring and heating at 90°~140° C. for about 4 hours. Meanwhile, the by-produced water was sufficiently removed.

After the completion of the reaction, the reaction mixture was neutralized with an aqueous solution of sodium hydroxide and the solvent toluene was recovered to obtain an aimed-at mixture of three kinds of esters (specimen No. 21).

Yield=98.0%, acid value=1.48, saponification value=121.36, pH (1%)=5.69, the molar ratio of the group A ester, group B ester and group C ester (%)=15:0:25.

Blending Examples 1~21

The compounds A~Q obtained in Preparation Examples 1~17 were mixed in the ratios shown in Table 2 to obtain blended compositions of specimens Nos. 1~18. The mixtures obtained in Preparation Example 18~20 are indicated as specimens Nos. 19~21 the same table.

The compositions and physical properties of the specimens are also shown in Tables 2~4.

TABLE 2

Composition of alcohol and kind of acyl group of each specimen

| | Specimen No. | Composition ratio (mol %) Liquid higher alkyl or alkenyl alcohol | Solid higher alkyl alcohol | Sterol | Acyl group | \multicolumn{17}{c}{Mixing ratio of compounds} |
|---|---|---|---|---|---|---|---|---|---|---|---|---|---|---|---|---|---|---|---|---|---|
| | | | | | | A | B | C | D | E | F | G | H | I | J | K | L | M | N | O | P | Q |
| Examples | 1 | 2-Octyldodecanol | — 50:50 | Cholesterol | Lauroyl | 1 | | 3 | | | | | | | | | | | | | 1 | |
| | 2 | 2-Octyldodecanol | — 75:25 | Cholesterol | Lauroyl | | | 5 | | | | | | | | | | | | | 5 | |
| | 3 | 2-Octyldodecanol | Behenyl alcohol 50:20:30 | Cholesterol | Lauroyl | | | 4 | 2 | | | | | | | | | | | | 4 | |
| | 4 | 2-Octyldodecanol | Behenyl alcohol 40:25:35 | Cholesterol | Lauroyl | 1 | | 4 | 2 | | | | | | | | | 1 | | 2 | 2 | |
| | 5 | 2-Octyldodecanol | Behenyl alcohol 75:10:15 | Cholesterol | Lauroyl | 1 | | 2 | | | | | | | | | | | | 5 | 5 | |
| | 6 | 2-Octyldodecanol* | Behenyl alcohol 50:40:10 | Cholesterol | Lauroyl | | | 1 | | | | | | | | | | | | | 1 | 3 |
| | 7 | 2-Octyldodecanol | — 50:50 | Cholesterol | Stearoyl | | | | | | | | 1 | | | | | | | | | |
| | 8 | 2-Octyldodecanol | Behenyl alcohol 50:20:30 | Phytosterol | Lauroyl | | | | | | | | | | 2 | | 1 | | | | 2 | |
| | 9 | 2-Octyldodecanol | Behenyl alcohol 50:20:30 | Dihydrocholesterol | Lauroyl | | | | | | | | | | 2 | | 1 | | | | 2 | |
| | 10 | 2-Octyldodecanol | Behenyl alcohol 60:10:30 | Cholesterol | Stearoyl | | | | | | 1 | 2 | | | | | | | | | 1 | 1 |
| | 11 | 2-Octyldodecanol* | Behenyl alcohol 25:55:20 | Cholesterol | Lauroyl | | | 2 | | | | | | | | | | 3 | | 1 | | 2 |
| | 12 | 2-Octyldodecanol | Behenyl alcohol 15:35:50 | Cholesterol | Lauroyl | 1 | | 3 | 1 | | | | | | | | | 1 | | 1 | | |
| | 13 | 2-Octyldodecanol | Behenyl alcohol 20:10:70 | Cholesterol | Lauroyl | | 2 | 1 | 2 | | | | | | | | | | | | | |
| | 14 | 2-Octyldodecanol | Behenyl alcohol 60:10:30 | Cholesterol | Lauroyl | | | 1 | 2 | | | | | | | | | | | | 2 | |
| | 15 | — | — 0:0:100 | Cholesterol | Lauroyl | 1 | | | | | | | | | | | | | | | | |
| Comparative Examples | 16 | 2-Octyldodecanol* | Behenyl alcohol 50:50:0 | | Lauroyl | | | | | | | | | | | | | | | | | 1 |
| | 17 | — | Behenyl alcohol 0:100:0 | — | Lauroyl | | | | | | | | | | | | | | 1 | | | |
| | 18 | 2-Octyldodecanol | — 100:0:0 | — | Lauroyl | | | | | | | | | | | | | | | | 1 | |
| Examples | 19 | 2-Octyldodecanol | Behenyl alcohol 50:20:30 | Cholesterol | Lauroyl | | | | | | | | | | | | | | | | | |
| | 20 | 2-Octyldodecanol | Behenyl alcohol 60:10:30 | Cholesterol | Stearoyl | | | | | | | | | | | | | | | | | |
| | 21 | 2-Octyldodecanol | — 75:0:25 | Cholesterol | Lauroyl | | | | | | | | | | | | | | | | | |

TABLE 3

Physical property and nature of amino acid type sterol ester

| Specimen No. | Acid value | Saponification value | Nature |
|---|---|---|---|
| 1 | 3.76 | 113.59 | Viscous clouded liquid |
| 2 | 1.48 | 121.36 | Viscous clear liquid |
| 3 | 3.06 | 121.87 | Soft clouded paste |
| 4 | 2.38 | 118.84 | Soft wax |

TABLE 3-continued

Physical property and nature of amino acid type sterol ester

| Specimen No. | Acid value | Saponification value | Nature |
|---|---|---|---|
| 5 | 2.42 | 122.51 | Soft clouded paste |
| 6 | 1.37 | 124.35 | Soft wax |
| 7 | 3.20 | 108.98 | Viscous clouded liquid |
| 8 | 3.34 | 119.41 | Soft paste |
| 9 | 2.83 | 120.39 | Soft paste |
| 10 | 1.25 | 106.23 | Soft paste |
| 11 | 3.42 | 115.71 | Wax |
| 12 | 3.12 | 111.53 | Wax |
| 13 | 2.83 | 112.03 | Viscous paste |
| 14 | 2.68 | 105.49 | Soft clouded paste |
| 15 | 4.52 | 105.21 | Wax |
| 16 | 3.74 | 123.78 | Wax |
| 17 | 1.28 | 117.63 | Wax |
| 18 | 3.57 | 127.40 | Liquid |
| 19 | 3.06 | 121.87 | Soft paste |
| 20 | 4.25 | 106.23 | Soft paste |
| 21 | 1.48 | 121.36 | Viscous liquid |

TABLE 4

Solubility of amino acid type sterol ester (2%, 30° C.)

| Specimen No. | Water | Propylene glycol | Ethanol | Olive oil | Castor oil | Liquid paraffin |
|---|---|---|---|---|---|---|
| 1 | I | I | S | S | S | S |
| 2 | I | I | S | S | S | S |
| 3 | I | I | S | S | S | S |
| 4 | I | I | S | S | S | S |
| 5 | I | I | S | S | S | S |
| 6 | I | I | S | S | S | S |
| 7 | I | I | S | S | S | S |
| 8 | I | I | S | S | S | S |
| 9 | I | I | S | S | S | S |
| 10 | I | I | S | S | S | S |
| 11 | I | I | S | S | S | S |
| 12 | I | I | S | S | S | S |
| 13 | I | I | S | S | S | S |
| 14 | I | I | S | S | S | S |
| 15 | I | I | S | S | S | S |
| 16 | I | I | S | S | S | S |
| 17 | I | I | S | S | S | S |
| 18 | I | I | S | S | S | S |
| 19 | I | I | S | S | S | S |
| 20 | I | I | S | S | S | S |
| 21 | I | I | S | S | S | S |

I: insoluble
S: soluble

Application examples will be shown below in which the blending ratio of the ingredients is based on the weight percentage.

Application Example 1 (O/W type cream)

The following ingredient (1) was warmed to 80° C. while the ingredient (2) was warmed to 50° C., and the ingredient (2) was gradually added to the ingredient (1) under stirring to emulsify. The ingredient (3) was added at 50° C. under stirring and water cooling and then cooled to 35° C. to prepare a product (Product A).

| Ingredient (1) | |
|---|---|
| Squalane | 8.0 |
| Cetyl octanate | 13.0 |
| Ester mixture of the invention (Specimen No. 5) | 10.0 |
| Hardened oil | 5.0 |
| Behenyl alcohol | 1.0 |
| Stearic acid | 2.0 |
| Self-emulsifiable glycerine monostearate | 4.0 |
| Diglycerine oleate | 1.0 |
| Dimethyl polysiloxane | 0.3 |

| Ingredient (2) | |
|---|---|
| Preservative | 0.2 |
| Sodium N-stearoyl-L-glutamate | 0.4 |
| Xanthane gum | 0.05 |
| 1,3-butylene glycol | 7.0 |
| Purified water | 47.85 |
| Ingredient (3) | |
| Perfume | 0.22 |
| | 100.0% |

An O/W type cream with luster of opaque color and having excellent emollient property and good feeling of use was obtained by blending the ester mixture according to the present invention (specimen No. 3).

Then, a comparative product (Product B) was prepared by using N-lauroyl-L-glutamic acid dioctyl dodecyl ester (Specimen No. 18) instead of the ester mixture of the present invention (Specimen No. 3) in the ingredients of Product A.

Then, a blind functional test was conducted using a panel of 40 adults of 18~26 years (20 men and 20 women).

The results are shown in Table 5.

TABLE 5

| | Test items | | | | | |
|---|---|---|---|---|---|---|
| | Spreadability | | Emollient property | | Feeling of use | |
| Product | Man | Woman | Man | Woman | Man | Woman |
| A | 17 | 18 | 18 | 20 | 17 | 19 |
| B | 3 | 2 | 2 | 0 | 3 | 1 |

*Numerical values in the table show the number of persons who judged best.

Between products A and B, satisfactory results were obtained for Product A with respect to all of the test items.

Further, the results of the test for the aging change of Product A and B are shown in Table 6.

TABLE 6

| | Number of days elapsed | | | |
|---|---|---|---|---|
| Product | 4 days | 7 days | 30 days | 60 days |
| A | ○ | ○ | ○ | ○ |
| B | ○ | △ | △ | X |

○: Stable emulsion.
△: Slight segregation observed.
X: Segregation and denaturation observed.
Emulsion stability (cycles of 40° C. (48 hr) ⇌ 0° C. (48 hr))

From the results, Product A shows satisfactory stability, whereas Product B is unsatisfactory.

As can be seen from the various tests described above, the ester mixture according to the present invention when incorporated into a cream can improve the cream in the performance such as spreadability, emollient property and feeling of use and, in addition, since it has excellent hydrating property and self-emulsifiability, the aging stability of products can also be improved.

An emollient cream quite in the same composition as in Product A except for blending Specimen No. 19 instead of Specimen No. 3 was prepared and the results obtained were substantially identical.

Application Example 2 (W/O type foundation cream)

The following ingredient (1) was warmed to 85° C. (The metallic soaps had been dissolved by heating to 90°~95° C.), while the following ingredient (2) was warmed to 85° C. The ingredient (2) was gradually added to the ingredient (1) under stirring to emulsify.

The ingredient (3) was added at 50° C. under cooling and stirring and then cooled to 35° C., to obtain a foundation cream (Product C).

| Ingredient (1) | |
| --- | --- |
| Squalane | 15.0 |
| Sericin | 3.0 |
| Bee wax | 1.0 |
| Jojoba oil | 3.0 |
| Ester mixture of the invention (Specimen No. 8) | 4.0 |
| Polyglycerine di-isostearate | 6.0 |
| Magnesium myristate | 1.0 |
| Aluminum stearate | 0.5 |
| Pigment | 15.0 |
| Ingredient (2) | |
| Preservative | 0.2 |
| Magnesium sulfate | 0.1 |
| Sorbitol | 5.0 |
| Sodium hyaluronate (1% aqueous solution) | 2.0 |
| Purified water | 44.0 |
| Ingredient (3) | |
| Perfume | 0.2 |
| | 100.0% |

As for the perfuming cosmetics of the present invention (Product C), since the ester mixture of the present invention (Specimen No. 8) is a strongly hydrating oil-soluble material, a W/O emulsion of excellent stability can be attained by blending the ester mixture. Further, the ester mixture of the present invention shows good dispersibility for titanium, talc or the like and can provide a W/O foundation cream of excellent skin affinity and depositability when the ester mixture in added.

Application Example 3 (milky lotion)

The following ingredient (1) was warmed to 85° C. and it was gradually added to the following ingredient (2) under stirring and then the following ingredient (3) was added. They were stirred under water cooling to obtain a milky lotion at 30° C. (Product D).

| ingredient (1) | |
| --- | --- |
| Squalane | 10.0 |
| Ester mixture of the invention (Specimen No. 5) | 3.0 |
| Isocetyl octanate | 9.0 |
| Glycerine trioctanate | 4.0 |
| Propylene glycol stearate | 0.5 |
| Behenyl alcohol | 0.5 |
| Stearic acid | 1.0 |
| Oleophilic glycerine monostearate | 1.0 |
| Diglycerine oleate | 0.5 |
| Polyethylene glycol stearate | 2.5 |
| Ingredient (2) | |
| Preservative | 0.2 |
| Carboxyvinyl polymer (1.0% aqueous solution) | 15.0 |
| Oleyl phosphoric acid | 0.4 |
| 1,3-butylene glycol | 5.0 |
| Purified water | 46.9 |
| Ingredient (3) | |
| L-arginine | 0.3 |
| Purified water | 0.2 |
| | 100.0% |

When the ester mixture of the invention (Specimen No. 5) was incorporated, an emulsion with fine emulsified particles and of excellent aging stability could obtained, and the skin affinity and depositability could can be improved by incorporating the ester mixture of the invention, to obtain an emulsion with good feeling of use.

Application Example 4 (Hair lotion)

The following ingredient (1) was warmed to 80° C. and the following ingredient (2) was warmed to 85° C. The ingredient (2) was gradually added to the ingredient (1) under stirring. The ingredient (3) was added to 50° C. while stirring under cooling and then the mixture was cooled to 35° C. to obtain a hair lotion (Product E).

| Ingredient (1) | |
| --- | --- |
| Liquid paraffin | 15.0 |
| Vaseline | 5.0 |
| Isopropyl myristate | 10.0 |
| Bee wax | 1.0 |
| Ester mixture of the invention (Specimen No. 1) | 10.0 |
| Stearic acid | 1.0 |
| Propylene glycol stearate | 1.0 |
| Polyglycerine oleate | 4.0 |
| Hydrogenated soy-bean lecithin | 1.0 |
| Ingredient (2) | |
| Preservative | 0.2 |
| Sodium N-stearoyl-L-glutamate | 0.4 |
| Xanthane gum (1.0% aqueous solution) | 10.0 |
| 1,3-butylene glycol | 5.0 |
| Purified water | 36.1 |
| Ingredient (3) | |
| Perfume | 0.3 |
| | 100.0% |

Since the ester mixture of the invention (Specimen No. 1) is a starting material having high compatibility with other starting materials such as hydrocarbon, wax and lecithin and having excellent emulsifying performance, products of high commercial value can be obtained. In addition, since the ester mixture of the invention has excellent performance such as affinity, depositability and moisture keeping property, hair cosmetics of high commercial value can be obtained.

Application Example 5 (Hair rinse)

The following ingredient (1) was warmed to 85° C. and the ingredient (2) was warmed to 80° C. The ingredient (1) was gradually added to the ingredient (2) under stirring. Then, the ingredient (3) was added at 50° C. while stirring under cooling, to obtain a hair rinse at 35° C. (Product F).

| Ingredient (1) | |
| --- | --- |
| Liquid paraffin | 2.0 |
| Ester mixture of the invention (Specimen No. 10) | 2.0 |
| Cetostearyl alcohol | 4.0 |
| Polyglycerine oleate | 1.0 |
| Alkyltrimethyl ammonium chloride | 3.0 |
| Polyoxyethylene glycerine pyroglutamate isostearate | 0.5 |
| Ingredient (2) | |
| Preservative | 0.1 |
| 1,3-butylene glycol | 8.0 |
| Purified water | 79.1 |
| Ingredient (3) | |
| Perfume | 0.3 |
| | 100.0% |

The ester mixture (Specimen No. 10) of the invention forms a complex compound together with a cationic surface active agent, higher alcohol or the like to increase the rinsing and conditioning effects, has good compatibility, for example, with cetanol and stearyl alcohol to be a crystallization inhibitor for high melting point materials at low temperatures.

Application Example 6 (Hair treatment cream)

The following ingredient (1) was warmed to 80° C., while the ingredient (2) was warmed to 85° C. The ingredient (2) was gradually added to the ingredient (1) under stirring. Then, the ingredient (3) was added at 50° C. while stirring under cooling, to obtain a product at 35° C. (Product G).

| Ingredient (1) | |
| --- | --- |
| Liquid paraffin | 9.0 |
| Cetyl octanate | 4.0 |
| Ester mixture of the invention (Specimen No. 7) | 4.0 |
| Cetostearyl alcohol | 5.0 |
| Propylene glycol stearate | 2.0 |
| Glycerine stearate | 1.0 |
| Polyethylene glycol stearate | 1.0 |
| Distearyldimethyl ammonium chloride | 1.0 |
| Ingredient (2) | |
| N-cocoyl-arginine-ethyl pyrrolidone carboxylate | 0.5 |
| 1,3-butylene glycol | 5.0 |
| Chitin (1.0% aqueous solution) | 10.0 |
| Purified water | 57.2 |
| Ingredient (3) | |
| Perfume | 0.3 |
| | 100.0% |

Since the ester mixture (Specimen No. 7) of the invention has good combatibility with oleo-phase starting material, for example, cationic surface active agent and higher alcohol and it also has excellent emulsifying performance, products in a good emulsified state and highly opaque nature can be obtained. In addition, since this is an amino type material, it can provide an excellent protecting effect for damaged hairs when used in combination with an amino acid type cationic surface active agent.

Then, a comparative product (Product H) was prepared by blending di-POE(2 mol)-stearyl ether N-lauroyl glutamate instead of the ester mixture of the invention (Specimen No. 7) in the ingredients of Product G (product of the invention) and a functional test was conducted.

The results are shown in the following Table 7.

TABLE 7

| Product | Spreadability upon use | Combing property | Smoothness | Moistened feeling | Luster |
| --- | --- | --- | --- | --- | --- |
| G | ⊚ | ⊚ | ⊚ | ⊚ | ⊚ |
| H | Δ | Δ | ○ | Δ | X |

⊚: particularly preferred
Δ: ordinary
○: preferred
X: poor

As apparent from Table 7, Product G provided good results with respect to all of the test items as compared with Product H.

Application Example 7 (Hair shampoo)

The following ingredients (1) and (2) were warmed to 80° C. and 85° C., respectively. The ingredient (2) was gradually added to the ingredient (1) while stirring. Then, the mixture was cooled and the ingredient (3) was added at 50° C. and the resultant mixture was cooled to 30° C., to obtain a shampoo (Product I).

| Ingredient (1) | |
| --- | --- |
| Triethanolamine N-cocoyl-L-glutamate (30% aqueous solution) | 20.0 |
| Sodium lauroyl methyl-β-alanine (30% aqueous solution) | 20.0 |
| Coconut oil fatty acid amide propyl betaine (30% aqueous solution) | 30.0 |
| Cationized cellulose | 0.5 |
| Propylene glycol | 5.0 |
| Preservative | 0.2 |
| Purified water | 13.0 |
| Ingredient (2) | |
| Coconut oil fatty acid diethanolamide | 4.0 |
| Polyoxyethylene glycerine triisostearate | 3.0 |
| Propylene glycol laurate | 2.0 |
| Ester mixture of the invention (Specimen No. 14) | 2.0 |
| Ingredient (3) | |
| Perfume | 0.3 |
| | 100.0% |

Since the ester mixture of the invention (Specimen No. 14) is an amino acid type derivative, it can give a shampoo having high hair affinity and depositability and a conditioning effect.

Application Example 8 (Cleansing foam)

The following ingredients (1) and (2) were warmed to 85° C. and 80° C., respectively. The ingredient (1) was gradually added to the ingredient (2) while stirring. Then, the ingredient (3) was added to 50° C. while cooling the mixture and the resultant mixture was further cooled to 35° C. to obtain a product (Product J).

| Ingredient (1) | |
| --- | --- |
| Ester mixture of the invention (Specimen No. 9) | 4.0 |
| Lauric acid | 3.0 |
| Myristic acid | 3.0 |
| Polyoxyethylene hardened caster oil | 2.0 |
| Coconut oil fatty acid diethanolamine | 8.0 |
| Ingredient (2) | |
| Sodium hydroxide | 0.8 |
| Polyethylene glycol | 15.0 |
| Propylene glycol | 15.0 |
| Sodium N-lauroyl-L-glutamate | 30.0 |
| Purified water | 19.0 |
| Ingredient (3) | |
| Perfume | 0.2 |
| | 100.0% |

When the ester mixture of the invention (Specimen No. 9) is used as a non-polar material for soap and cleansing foam of sodium N-acyl L-glutamate, it can prevent cracking of the soap and improve the creaminess of the cleansing cream. In addition, it can provide soap or cleansing foam products with excellent performance as a super fatting agent and an emollient agent.

Application Example 9 (Lip stick (1))

The following ingredient (1) was dissolved under heating substantially at 80° C and then mixed uniformly. The ingredient (2) was added, and the mixture was kneaded with a roll mill and uniformly dispersed. Then, the mixture was melted again, the ingredient (3) was added and, after defoaming, the resultant mixture was cast into a molding dye and solidified by quenching, to obtain a lip stick (1).

| Ingredient (1) | |
| --- | --- |
| Castor oil | 51.9 |

-continued

| | |
|---|---|
| Octyl dodecanol | 15.0 |
| Ester mixture of the invention (Specimen No. 19) | 5.0 |
| Liquid lanoline | 5.0 |
| Bee wax | 4.0 |
| Ozokerite | 5.0 |
| Candelilla wax | 7.0 |
| Carnauba wax | 2.0 |
| Ingredient (2) | |
| Titanium oxide | 1.0 |
| Red No. 201 | 1.0 |
| Red No. 202 | 2.0 |
| Yellow No. 4 aluminum lake | 1.0 |
| Red No. 223 | 0.1 |
| Ingredient (3) | |
| Perfume | appropriate amount |
| Antioxidant | appropriate amount |
| Preservative | appropriate amount |
| | 100.0% |

The resultant lip stick (1) was stable for a long period of time with no sweating. In addition, it had clear color and appropriate strength. Further, it had good affinity with skin and excellent spreadability.

Application Example 10 (Lip stick (2))

A lip stick (2) was obtained in the same way as in the lip stick (1) by using the following ingredients (1), (2) and (3).

| | |
|---|---|
| Ingredient (1) | |
| Ozokerite | 5.0 |
| Sericin | 5.0 |
| Solid paraffin | 10.0 |
| Ester mixture of the invention (Specimen No. 2) | 40.0 |
| Glycerine trioctanate | 20.0 |
| Octyldodecyl myristate | 10.0 |
| Ingredient (2) | |
| Titanium oxide | 1.0 |
| Red No. 201 | 1.0 |
| Red No. 202 | 1.0 |
| Blue No. 1 aluminum lake | 0.5 |
| Mica titanium | 6.5 |
| Ingredient (3) | |
| Perfume | appropriate amount |
| Antioxidant | appropriate amount |
| Preservative | appropriate amount |
| | 100.0% |

The resultant lip stick (2) got the same evaluation as in the lip stick (1).

Application Example 11 (Lip stick (3))

A lip stick (3) was prepared by using the following ingredients. That is, after mixing the oily substrates and then melting them under heating, the colorants previously mixed with castor oil and dissolved and dispersed homogeneously was admixed, to which the perfume and the antioxidant were added, and they were further mixed homogeneously under stirring. The liquid was cast into a molding die and rapidly cooled to obtain a lip stick (3).

| | |
|---|---|
| Bee wax | 10.0 |
| Sericin | 24.0 |
| Carnauba wax | 8.0 |

-continued

| | |
|---|---|
| Ester mixture of the invention (Specimen No. 15) | 10.0 |
| Liquid paraffin | 22.0 |
| Castor oil | 21.0 |
| Eosinic acid | 2.5 |
| Pigment | 1.0 |
| Perfume | 1.5 |
| Antioxidant | appropriate amount |
| | 100.0% |

The evaluation result for the resultant lip stick (3) was excellent like that as for the lip stick (1).

Application Example 12 (Powder foundation (1))

The following ingredient (1) was mixed and pulverized through a pulverizer. It was transferred to a high speed blender, mixed with the ingredients (2) and (3) and then added to a pigment and uniformly mixed. The mixture was treated by a pulverizer, conditioned for the grain size by passing through a sieve and then, compression molded to obtain a powder foundation (1).

| | |
|---|---|
| Ingredient (1) | |
| Red iron oxide | 3.0 |
| Yellow iron oxide | 2.5 |
| Black iron oxide | 0.5 |
| Nylon powder | 10.0 |
| Titanium oxide | 10.0 |
| Mica | 20.0 |
| Talc | 44.0 |
| Ingredient (2) | |
| Liquid paraffin | 5.0 |
| Octyl dodecyl myristate | 2.5 |
| Ester mixture of the invention (Specimen No. 19) | 2.5 |
| Ingredient (3) | |
| Preservative | appropriate amount |
| Perfume | appropriate amount |
| | 100.0% |

The resultant powder foundation (1) well fit with skin and was excellent in spreadability.

Application Example 13 (Powder foundation (2))

In the same procedures as those for the powder foundation (1), the following ingredients (1) and (2) were prepared respectively and compression molded to obtain a powder foundation (2).

| | |
|---|---|
| Ingredient (1) | |
| Titanium oxide | 9.0 |
| Zinc oxide | 9.0 |
| Kaoline | 47.0 |
| Talc | 20.0 |
| Yellow iron oxide | appropriate amount |
| Red iron oxide | appropriate amount |
| Ingredient (2) | |
| Surface active agent (sorbitane monooleate) | 5.0 |
| Ester mixture of the invention (Specimen No. 3) | 6.0 |
| 1,3-butylene glycol | 4.0 |
| Perfume | appropriate amount |
| | 100.0% |

The resultant powder foundation (2) got the same evaluation like that of the powder foundation (1) and it was excellent in spreadability.

Application Example 14 (Liquid foundation (1))

The following ingredients (1), (2) and (3) were mixed respectively under heating at 80° C. That is, the ingredient (2) was added to the ingredient (1), and then the ingredient (3) was added. Further, the ingredient (4) was added, gradually cooled to 40° C., and stirred for 5 min in a homomixer, to obtain a liquid foundation (1).

| Ingredient (1) | |
|---|---|
| Stearate acid | 3.0 |
| Isopropyl myristate | 9.0 |
| Liquid paraffin | 1.5 |
| Cetanol | 1.0 |
| Preservative | appropriate amount |
| Coloring pigment | 8.0 |
| Ester mixture of the invention (Specimen No. 21) | 2.0 |
| Ingredient (2) | |
| Triethanolamine | 1.5 |
| Water | 25.0 |
| Ingredient (3) | |
| Propylene glycol | 5.0 |
| Preservative | appropriate amount |
| Water | 29.0 |
| Ingredient (4) | |
| Bentonite (1% aqueous solution) | 15.0 |
| | 100.0% |

As the evaluation result of the resultant liquid foundation (1), it was found to be a liquid foundation having fresh feeling of use and giving a moistening effect to skin.

Application Example 15 (Liquid foundation (2))

The following ingredient (3) was thoroughly mixed and pulverized by passing through a pulverizer. As for the ingredient (2), purified water was heated to 70° C., and bentonite was added and thoroughly swollen, to which sodium carboxymethyl cellulose previously dispersed in propylene glycol was added and dissolved. Triethanolamine and methyl p-oxybenzoate were added and dissolved. The ingredient (1) was mixed and melted under heating at 70°~80° C. The thus processed ingredient (3) was added under stirring to the thus processed ingredient (2). Subsequently, the mixture was passed through a colloid mill, heated again at 75° C. and then added to the ingredient (1) at 80° C. under stirring and then cooled. Then, the ingredient (4) was added at 45° C. and continuously stirred under cooling to room temperature, to obtain a liquid foundation (2).

| Ingredient (1) | |
|---|---|
| Stearic acid | 2.4 |
| Propylene glycol monostearate | 2.0 |
| Cetostearyl alcohol | 0.2 |
| Ester mixture of the invention (Specimen No. 3) | 2.0 |
| Liquid paraffin | 3.0 |
| Isopropyl myristate | 8.5 |
| Propyl p-oxybenzoate | appropriate amount |
| Ingredient (2) | |
| Water | 64.1 |
| Sodium carboxymethyl cellulose | 0.2 |
| Bentonite | 0.5 |
| Propylene glycol | 4.0 |
| Triethanolamine | 1.1 |
| Methyl p-oxybenzoate | appropriate amount |
| Ingredient (3) | |
| Titanium oxide | 8.0 |
| Talc | 4.0 |
| Coloring pigment | appropriate amount |
| Ingredient (4) | |
| Perfume | appropriate amount |
| | 100.0% |

The evaluation result for the obtained liquid foundation (2) was excellent like that for the liquid foundation (1).

Application Example 16 (Hair mousse)

The following ingredients (1) and (2) were dissolved by warming to 45° C., respectively. The ingredient (1) was added to the ingredient (2) under stirring. The mixture was stirred under cooling, to which the ingredient (3) was added at 40° C. and, after cooling to room temperature, the resultant base was transferred to an aerosol vessel and the ingredient (4) was further charged to produce a product.

| Ingredient (1) | |
|---|---|
| Liquid paraffin | 2.5 |
| Ester mixture of the invention (Specimen No. 19) | 2.0 |
| Polyoxyethylene lauryl ether | 1.0 |
| Ethyl alcohol | 15.0 |
| Ingredient (2) | |
| Glycerine | 10.0 |
| Propylene glycol | 1.0 |
| Water-soluble polymer | 2.0 |
| Water | 51.2 |
| Ingredient (3) | |
| Perfume | 0.3 |
| Ingredient (4) | |
| Propellant (LPG gas) | 15.0 |
| | 100.0% |

Foaming performance of hair mousse products can be improved by blending the ester mixture of the present invention. Products having excellent hair affinity and emollient property can be obtained.

What is claimed is:

1. An oil-soluble N-long chained acyl acidic amino acid mono- or di-ester represented by the following general formula (I):

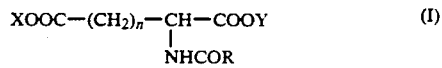

$$XOOC-(CH_2)_n-CH-COOY \quad (I)$$
$$| $$
$$NHCOR$$

where each of X and Y, which may be identical with or different from each other, represents an ester forming residue of cholesterol or dihydrocholesterol, or one of X and Y represents an ester forming residue of cholesterol or dihydrocholesterol and the other of them represents H, an ester forming residue of a liquid higher alkyl or alkenyl mono-hydric alcohol with 8 to 30 carbon atoms or a solid higher alkyl mono-hydric alcohol with 12 to 38 carbon atoms, COR represents a long chained acyl group with 8 to 22 carbon atoms and n is 1 or 2.

* * * * *